(12) United States Patent
Perlin

(10) Patent No.: US 11,385,955 B1
(45) Date of Patent: Jul. 12, 2022

(54) METHOD, APPARATUS AND COMPUTER SOFTWARE PROGRAM FOR DETERMINING PROBABILITY OF ERROR IN IDENTIFYING EVIDENCE

(71) Applicant: Mark W. Perlin, Pittsburgh, PA (US)

(72) Inventor: Mark W. Perlin, Pittsburgh, PA (US)

(*) Notice: Subject to any disclaimer, the term of this patent is extended or adjusted under 35 U.S.C. 154(b) by 15 days.

(21) Appl. No.: 16/691,063

(22) Filed: Nov. 21, 2019

Related U.S. Application Data

(63) Continuation-in-part of application No. 15/223,666, filed on Jul. 29, 2016, now Pat. No. 10,489,233.

(51) Int. Cl.
| | |
|---|---|
| *G06F 11/07* | (2006.01) |
| *G06N 7/00* | (2006.01) |
| *G06Q 40/00* | (2012.01) |
| *G06Q 90/00* | (2006.01) |

(52) U.S. Cl.
CPC .......... *G06F 11/079* (2013.01); *G06F 11/073* (2013.01); *G06N 7/005* (2013.01); *G06Q 40/00* (2013.01); *G06Q 90/00* (2013.01)

(58) Field of Classification Search
CPC ..... G06F 11/079; G06F 11/073; G06Q 40/00; G06Q 90/00
See application file for complete search history.

(56) References Cited

U.S. PATENT DOCUMENTS

| | | | | |
|---|---|---|---|---|
| 2005/0143629 A1* | 6/2005 | Farwell | .................. | A61B 5/164 600/300 |
| 2015/0347841 A1* | 12/2015 | Mears | .................... | G06V 40/70 348/46 |

* cited by examiner

*Primary Examiner* — Nadeem Iqbal
(74) *Attorney, Agent, or Firm* — Ansel M. Schwartz

(57) ABSTRACT

An apparatus for determining probability of error in identifying evidence includes a computer. The apparatus includes a non-transitory memory in communication with the computer in which is stored a software program, and prior and posterior probability distributions from a plurality of independent tests conducted on an item of evidence. For each test, the computer forms a factor distribution from the test's probability distributions using the software program stored in the non-transitory memory of the computer. The computer convolves the independent factor distributions to form a joint factor distribution using the software program. The computer calculates a tail probability from the joint factor distribution using the software program to determine a probability of error in identifying the evidence. The computer stores the probability of error in the non-transitory memory. A method. A computer program.

5 Claims, 6 Drawing Sheets

METHOD, APPARATUS AND COMPUTER SOFTWARE PROGRAM FOR DETERMINING PROBABILITY OF ERROR IN IDENTIFYING EVIDENCE

CROSS-REFERENCE TO RELATED APPLICATIONS

This is a divisional of U.S. patent application Ser. No. 15/223,666 filed Jul. 29, 2016, now U.S. Pat. No. 10,489,233, incorporated by reference herein.

FIELD OF THE INVENTION

The present invention is related to determining probability of error in identifying evidence. More specifically, the present invention is related to determining probability of error in identifying evidence, by convolving independent factor distributions to form a joint factor distribution and calculating a tail probability from the joint factor distribution with a computer.

BACKGROUND OF THE INVENTION

Statistical computing can provide an accurate match statistic for forensic identification. The resulting likelihood ratio (LR) quantifies the probative force of evidence, capturing in a single number the strength of match. But the LR may be difficult to explain to a non-statistician. Nor does the LR convey the chance of error, often a juror's foremost concern.

Error can be expressed as a false match probability (FMP). With biological evidence, a false match occurs when someone's DNA is not present, but has a match statistic at least as large as the reported LR. FMP is the chance of this misidentification occurring.

This invention shows how to rapidly and accurately calculate the FMP. The approach permits FMP evaluation on very large sets, and provides sharper error estimates than the guaranteed 1/LR upper bound. Mathematical theory is presented, along with a DNA case example of sexual assault and database search. By reporting exact error rates on specific evidence data, FMP assists investigators, scientists, lawyers, jurors and judges in their forensic decision-making.

SUMMARY OF THE INVENTION

The present invention pertains to a method for determining probability of error in identifying evidence. The method comprises the steps of obtaining prior and posterior probability distributions from a plurality of independent tests conducted on an item of evidence. There is the step of entering the probability distributions into a non-transitory memory of a computer. There is the step of, for each test, forming a factor distribution from the test's probability distributions with the computer using a software program stored in the non-transitory memory of the computer. There is the step of convolving the independent factor distributions to form a joint factor distribution by the computer using the software program. There is the step of calculating a tail probability from the joint factor distribution by the computer using the software program to determine a probability of error in identifying the evidence. There is the step of storing the probability of error in the non-transitory memory of the computer. There is the step of reporting the probability of error from the computer to a party interested in identifying the evidence.

The present invention pertains to a computer program stored in a non-transitory memory for determining probability of error in identifying evidence by obtaining prior and posterior probability distributions from a plurality of independent tests conducted on an item of evidence and entering the probability distributions into a non-transitory memory of a computer, the computer program comprising the computer implemented steps using the computer program of, for each test, forming a factor distribution from the test's probability distributions with the computer. There is the step of convolving the independent factor distributions to form a joint factor distribution by the computer. There is the step of calculating a tail probability from the joint factor distribution by the computer to determine a probability of error in identifying the evidence. There is the step of storing the probability of error in the non-transitory memory of the computer. There is the step of reporting the probability of error from the computer to a party interested in identifying the evidence.

The present invention pertains to an apparatus for determining probability of error in identifying evidence. The apparatus comprises a computer. The apparatus comprises a non-transitory memory in communication with the computer in which is stored a software program, and prior and posterior probability distributions from a plurality of independent tests conducted on an item of evidence. For each test, the computer forms a factor distribution from the test's probability distributions using the software program stored in the non-transitory memory of the computer. The computer convolves the independent factor distributions to form a joint factor distribution using the software program. The computer calculates a tail probability from the joint factor distribution using the software program to determine a probability of error in identifying the evidence. The computer stores the probability of error in the non-transitory memory. The apparatus comprises a printer 18 in communication with the computer which prints out a report that reports the probability of error to a party interested in identifying the evidence, or a display in communication with the computer on which the computer displays the report.

The present invention pertains to a method for determining probability of error in identifying evidence. The method comprises the steps of obtaining prior and posterior probability distributions conducted on an item of evidence. There is the step of entering the probability distributions into a non-transitory memory of a computer. There is the step of examining the probabilities of at least a trillion possible outcomes. There is the step of forming a factor distribution from the probability distributions on the examined outcomes with the computer using a software program stored in the non-transitory memory of the computer.

DETAILED DESCRIPTION OF THE INVENTION

The present invention pertains to a method for determining probability of error in identifying evidence. The method comprises the steps of obtaining prior and posterior probability distributions from a plurality of independent tests conducted on an item of evidence. There is the step of entering the probability distributions into a non-transitory memory 14 of a computer 12. There is the step of, for each test, forming a factor distribution from the test's probability distributions with the computer 12 using a software program 16 stored in the non-transitory memory 14 of the computer 12. There is the step of convolving the independent factor distributions to form a joint factor distribution by the computer 12 using the software program 16. There is the step of calculating a tail probability from the joint factor distribution by the computer 12 using the software program 16 to determine a probability of error in identifying the evidence. There is the step of storing the probability of error in the non-transitory memory 14 of the computer 12. There is the step of reporting the probability of error from the computer 12 to a party interested in identifying the evidence.

The present invention pertains to a computer 12 program stored in a non-transitory memory 14 for determining probability of error in identifying evidence by obtaining prior and posterior probability distributions from a plurality of independent tests conducted on an item of evidence and entering the probability distributions into a non-transitory memory 14 of a computer 12, the computer 12 program comprising the computer 12 implemented steps using the computer 12 program of, for each test, forming a factor distribution from the test's probability distributions with the computer 12. There is the step of convolving the independent factor distributions to form a joint factor distribution by the computer 12. There is the step of calculating a tail probability from the joint factor distribution by the computer 12 to determine a probability of error in identifying the evidence. There is the step of storing the probability of error in the non-transitory memory 14 of the computer 12. There is the step of reporting the probability of error from the computer 12 to a party interested in identifying the evidence.

Figure 6:
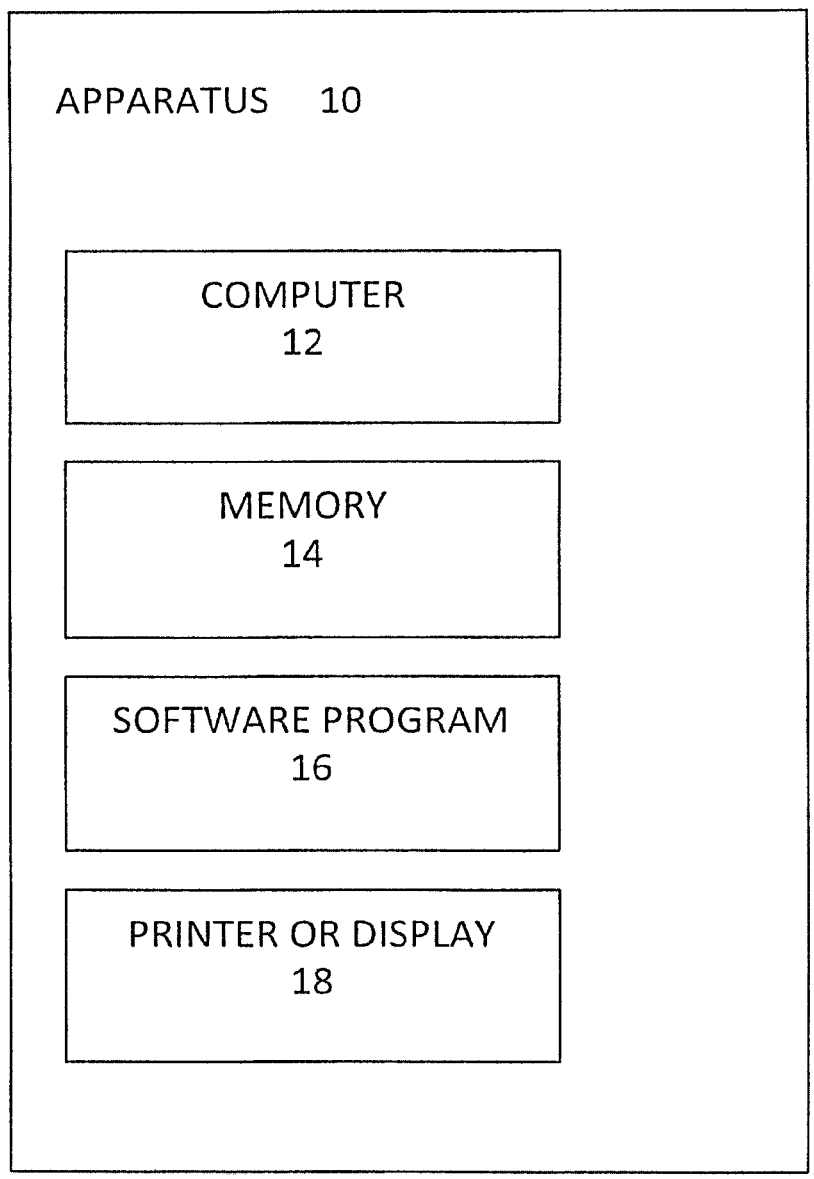
FIG. 6 is a block diagram of the apparatus of the present invention.

The present invention pertains to an apparatus 10 for determining probability of error in identifying evidence, as shown in FIG. 6. The apparatus 10 comprises a computer 12. The apparatus 10 comprises a non-transitory memory 14 in communication with the computer 12 in which is stored a software program 16, and prior and posterior probability distributions from a plurality of independent tests conducted on an item of evidence. For each test, the computer 12 forms a factor distribution from the test's probability distributions using the software program 16 stored in the non-transitory memory 14 of the computer 12. The computer 12 convolves the independent factor distributions to form a joint factor distribution using the software program 16. The computer 12 calculates a tail probability from the joint factor distribution using the software program 16 to determine a probability of error in identifying the evidence. The computer 12 stores the probability of error in the non-transitory memory 14. The apparatus 10 comprises a printer 18 in communication with the computer 12 which prints out a report that reports the probability of error to a party interested in identifying the evidence, or a display in communication with the computer 12 on which the computer 12 displays the report.

The present invention pertains to a method for determining probability of error in identifying evidence. The method comprises the steps of obtaining prior and posterior probability distributions conducted on an item of evidence. There is the step of entering the probability distributions into a non-transitory memory 14 of a computer 12. There is the step of examining the probabilities of at least a trillion possible outcomes. There is the step of forming a factor distribution from the probability distributions on the examined outcomes with the computer 12 using a software program 16 stored in the non-transitory memory 14 of the computer 12.

After the forming step, there may be the additional steps of:

e. Calculating a tail probability from the factor distribution by the computer 12 using the software program 16 to determine a probability of error in identifying the evidence;

f. Storing the probability of error in the non-transitory memory 14 of the computer 12; and g. Reporting the probability of error from the computer 12 to a party interested in identifying the evidence.

The examining step may take no more than one minute of computer 12 time. The factor may be related to a likelihood ratio. The factor may be used for forensic identification. The item may be biological evidence. The tests may involve DNA analysis. The item may be fingerprint evidence. The item may be firearm evidence. The factor distribution may provide exclusionary information about the evidence. They factor distribution they provide inclusionary information about the evidence. The probability of error may help identify an investigative lead. They probability of error may assist a trier of fact in understanding the evidence. The test may conduct a biometric measurement. The test may be for a genetic disease. The test may be for determining parentage. The factor may assist a physician in assessing an outcome of a diagnostic test.

In the operation of the invention, it is often desired to compare a questioned item Q with a known exemplar K, and measure a degree of association between them. For example, one might want to pick out a known face from a large crowd. Or, have the Shazzam app recognize a song that is playing. Forensic scientists compare questioned DNA evidence with a genotype from a known person to calculate a numerical match statistic.

The concern here is the error in this numerical association. How often is this association wrong? Specifically, what is the chance that a random (hence incorrect) exemplar might have an association strength at least as large as the number observed?

Suppose each known exemplar corresponds to a certain type and that it can determined the type of a questioned item up to probability. Let X be the set of all possible types.

In a population, each type appears with some frequency. Let p(x) be the probability $Pr\{x \in X\}$ of type x appearing in the population. Prior probability p(x) is also the chance that a questioned item has type x, before examining data.

Informative data changes ones belief in an item's type (O'Hagan and Forster 2004). After examining data from a questioned item, q(x) is the posterior probability $Pr\{x \in X | data\}$ that the item is of type x.

The Bayes factor, or just factor $f(x)$, is the posterior to prior probability ratio q(x)/p(x). For any known type $x_K$, the factor $\alpha = f(x_K)$ expresses how much more a questioned item Q matches a known exemplar K than coincidence. The numerical association $f(x)$ is a likelihood ratio (Good 1950), which measures the probative force of evidence and factors out prior prejudice.

The error set $E_\alpha$ is the subset of types $\{x \in X | f(x) \geq \alpha\}$ for which the factor $f(x)$ equals or exceeds factor $\alpha$. When $\alpha = f(x_K)$ corresponds to a known exemplar K, $E_\alpha$ describes all the types x whose numerical association $f(x)$ with questioned item Q is at least as great as with $x_K$.

The size of this error set $E_\alpha$, relative to the random population p(x) distribution is of interest. The false match probability (FMP) $\Pr\{x \in E_\alpha\}$ is the sum $$\sum_{x \in E_\alpha} p(x)$$

of prior probabilities p(x) taken over all types in the error set $E_\alpha$. A small error probability indicates a small chance of a false positive that erroneously associates an exemplar type with a questioned item.

When examining questioned DNA evidence Q, comparison is made between an evidence genotype and a known exemplar genotype K to calculate a match statistic $\alpha = f(x_K)$. The FMP $\Pr\{x \in E_\alpha\}$ measures the chance of falsely matching someone who did not contribute their DNA to the evidence. This can happen when their genotype x has a match statistic $f(x)$ that coincidentally reaches or exceeds match level $\alpha$.

A contributor is a person who contributed their DNA to biological evidence. Contributor types follow the posterior probability distribution q(x). A non-contributor is someone who did not contribute DNA to biological evidence. Non-contributor types follow the prior probability distribution p(x).

Other forensic scientists have estimated FMP computationally (Gill, Curran et al. 2008; Slooten and Egeland 2015). Some have approximated the likelihood ratio distribution (Nothnagel, Schmidtke et al. 2010; Corradi and Ricciardi 2013). Monte Carlo simulation can count how frequently randomly generated genotypes exceed a reported match level (Slooten and Egeland 2014). Branch and bound algorithms help prune the search when genotype error set $E_\alpha$ is small (Dørum, Bleka et al. 2014), while divide and conquer methods can extend the search to larger sets (Kruijver 2015). When genotyping systems consider all possible allele values independently of the data (Perlin, Legler et al. 2011) the search space may increase exponentially beyond the range of such combinatorial methods. Some scientists avoid FMP altogether, either by using a generic LR upper bound (Taylor, Buckleton et al. 2015), or by electing to not report LR error (Kruijver, Meester et al. 2015; Taroni, Bozza et al. 2016).

This paper describes how to rapidly and accurately calculate the false match probability $\Pr\{x \in E_\alpha\}$. For concreteness, the presentation will describe the discrete genotypes used in DNA identification, and their probability mass functions (pmf). However, the approach is entirely general, and works with any measurable set X having measurable probability functions (Wheeden and Zygmund 1977), or with multi-dimensional tuples of types.

Starting with a natural upper bound on the size of the type error set $E_\alpha$. Then a logarithmic non-contributor distribution for factor $f(x)$ is examiner, showing how to exactly calculate the size of $E_\alpha$. The contributor distribution is also reviewed, and some useful population genetics correction factors. The error method is empirically verified, and its use in forensic DNA casework is shown.

Reciprocal Match Bound

It is always true that the FMP $\Pr\{x \in E_\alpha\}$ cannot exceed the reciprocal match statistic $1/\alpha$. This well-known fact follows from Markov's Inequality in elementary probability theory (Feller 1968), and the definition of the factor $f(x)$ as $q(x)/p(x)$ (Good 1950), as shown here.

The FMP $\Pr\{x \in E_\alpha\}$ is the total prior probability mass $$\sum_{x \in E_\alpha} p(x)$$

in the error set $E_\alpha = \{x \in X | f(x) \geq \alpha\}$. That is, $$\Pr\{x \in E_a\} = \sum_{x \in E_\alpha} p(x)$$

Since $f(x) \geq \alpha$ for every $x \in E_\alpha$, yields $$\leq \frac{1}{\alpha} \sum_{x \in E_\alpha} f(x) \cdot p(x) \qquad (1)$$

Writing the factor $f(x)$ explicitly as the posterior to prior ratio $$q(x)/p(x) = \frac{1}{\alpha} \sum_{x \in E_\alpha} \frac{q(x)}{p(x)} \cdot p(x)$$

and cancelling the positive prior probability p(x) appearing in both numerator and denominator leaves $$= \frac{1}{\alpha} \sum_{x \in E_\alpha} q(x)$$

Clearly the partial sum of positive probabilities q(x) over the error set $\{x \in E_\alpha\}$ cannot exceed the total sum over all genotypes $x \in X$, since $E_\alpha \subseteq X$, yielding the inequality $$(2) \leq \frac{1}{\alpha} \sum_{x \in X} q(x)$$

But the total probability $$\sum_{x \in X} q(x)$$

must be 1, yielding $$= \frac{1}{\alpha}$$

This establishes that the FMP is always bounded above by the reciprocal of the match statistic, or $$Pr\{x \in E_\alpha\} \leq \frac{1}{\alpha}$$

This upper bound provides a useful measure theoretic (or "frequentist") observation for a Bayesian match statistic. After comparing questioned evidence having probability function q(x) with a known exemplar $x_K$ to calculate a match statistic $\alpha = f(x_K)$, one can always state: "the chance that a non-contributor has a match statistic of at least $\alpha$ is no more than $1/\alpha$." So the statement tells us that the frequency of making a false positive match statistic error is inherently bounded by the reciprocal of the match statistic.

The upper bound of $1/\alpha$ is inexact because of two inequalities in the derivation. The first inequality (1) occurs because within error set $E_\alpha$ yields $$\alpha = \min_{E_\alpha} f \leq f(x),$$

and so $$\left(\min_{E_\alpha} f\right) \sum_{x \in E_\alpha} p(x) = \sum_{x \in E_\alpha} \alpha \cdot p(x) \leq \sum_{x \in E_\alpha} f(x) \cdot p(x).$$

Dividing through by the prior probability mass $$\sum_{x \in E_\alpha} p(x)$$

to obtain an average value of the factor $f$ on subset $E_\alpha$, yields $$\alpha = \min_{E_\alpha} f \leq \frac{\sum_{x \in E_\alpha} f(x) \cdot p(x)}{\sum_{x \in E_\alpha} p(x)} = \operatorname*{avg}_{E_\alpha}_p f$$

That is, on the error set $E_\alpha$, the smallest match statistic $$\min_{E_\alpha} f$$

is less than or equal to the average prior-weighted match statistic $$\operatorname*{avg}_{E_\alpha}_p f.$$

So when there is a long non-contributor $\alpha$ tail, with min $f$ □ $\operatorname{avg}_p f$ on error set $E_\alpha$, there is scope for improving the error bound from $1/\alpha$ to a smaller number.

The second inequality (2) relates to posterior probability mass on error subset $E_\alpha$, relative to all genotype possibilities X $$\operatorname*{sum}_{x \in E_\alpha} q(x) = \sum_{x \in E_\alpha} q(x) \leq \sum_{x \in X} q(x) = 1$$

With a short contributor $\alpha$ tail, having total mass $$\operatorname*{sum}_{E_\alpha} q \square 1$$

on error set $E_\alpha$, the error bound on the match statistic can be further reduced.

These inequalities highlight opportunities for sharpening the error estimate $Pr\{x \in E_\alpha\}$. Rather than stopping at the match statistic reciprocal $1/\alpha$ (Taylor, Buckleton et al. 2015), a more thorough error analysis customizes the FMP to the evidence. This analysis invites further study of the $f(x)$ factor distribution under prior (i.e., non-contributor) and posterior (i.e., contributor) probability assumptions. As shown next, this closer examination provides an exact calculation of the FMP.

Non-Contributor Distribution

Logarithmic Factor

The logarithm of the Bayes factor is a standard additive measure of information (MacKay 2003). Additivity aids in understanding, visualizing, computing, combining and characterizing the match statistic. The logarithmic distribution of match values for non-contributor genotypes that follow the prior probability distribution is examined here.

For each genotype $x \in X$, the match statistic is the Bayes factor $f(x) = q(x)/p(x)$. The logarithm of this function is $\log[q(x)/p(x)]$, dubbed the "weight of evidence," and for base 10 measured in "ban" units (Good 1950). It is desired to see how these logarithmic values are distributed according to prior distribution p(x) for non-contributors—random people in the population who have not contributed their DNA to the biological evidence. This amounts to studying the deposition of ordered pairs ($\log q(x)/p(x), p(x)$) for every genotype $x \in X$ as points on a two dimensional graph.

Single Locus

At a single genetic locus, genotype x is a pair of inherited alleles. Since the log factor $\log f(x)$ is the logarithm of a ratio q(x)/p(x), attention is restricted to those genotypes x having prior denominator $p(x) > 0$ and posterior numerator $q(x) > 0$, giving a well-defined value. Each well-defined genotype $x \in X$ adds a y-axis ordinate amount p(x) to the non-contributor distribution at x-axis abscissa location $\log f(x)$.

Adding together all the ordinate p(x) probability amounts at abscissa location $y = \log f(x)$ gives the total probability mass at one point $$u(y) = \sum_{\{x \in X | y = \log f(x)\}} p(x)$$

More compactly, since $\log f^{-1}(y)$ is the set of genotypes $\{x \in X | y = \log f(x)\}$ having log factor value y, the non-contributor probability mass function can be written as $$u(y) = \sum_{x \in \log f^{-1}(y)} p(x)$$

The accumulation of probability mass for the log $f$ distribution is shown in the Table 1 example. Each genotype possibility ($x_1$, $x_2$, $x_3$, $x_4$) is listed in the first column. The prior $p(x)$ and posterior $q(x)$ probabilities, before and after having seen data, respectively, are given in the next two columns. The Bayes factor $f(x)$ column contains the posterior-to-prior ratio $q(x)/p(x)$ of the preceding two columns. The last column is the logarithmic factor $\log f(x)$. The log factor is negative for exclusionary results where $f(x)<1$, positive for inclusionary results with $f(x)>1$, and zero when the factor $f(x)$ for genotype x is inconclusive.

Figure 1:
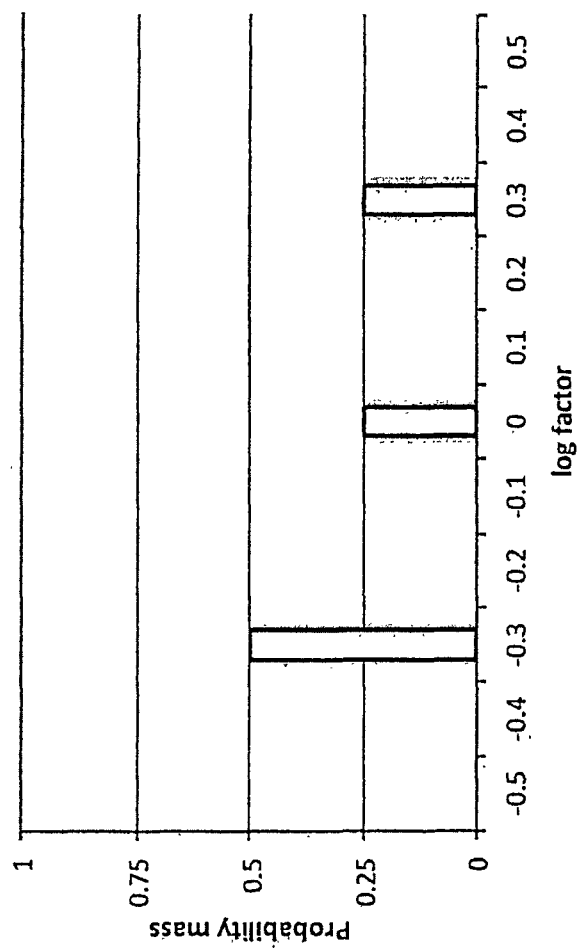
FIG. 1 is a Histogram of binned (log $f(x),p(x)$) pairs at a locus that constructs a probability mass function.
Figure 2:
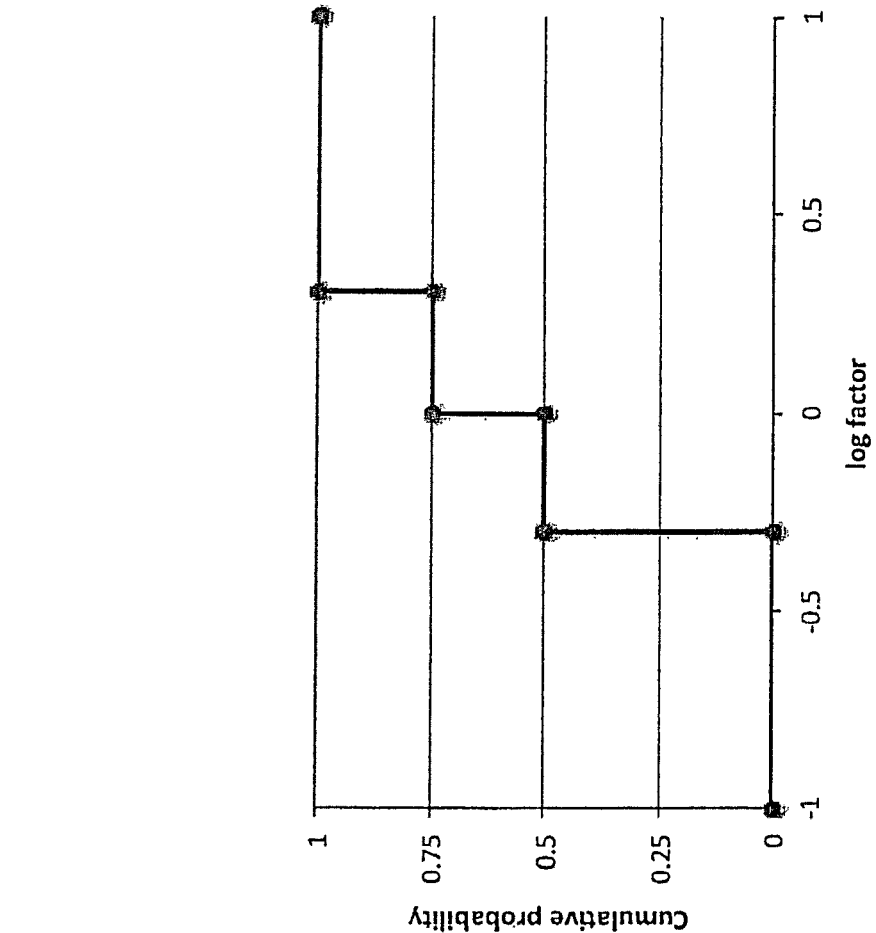
FIG. 2 shows cumulative probability at a locus represents a log factor distribution.

The FIG. 1 histogram shows ($\log f(x)$, $p(x)$) table row pairs binned at a deciban (i.e., 1/10 of a ban) resolution. Since log of ½ is around −0.3, bin "−0.3" adds together the $p(x_1)=0.2$ and $p(x_2)=0.3$ prior probabilities for non-contributor genotypes $x_1$ and $x_2$. Genotype $x_3$ has a factor of 1, hence a zero log factor, placing a $p(x_3)$ probability mass of 0.25 in bin "0". For genotype $x_4$, $q(x_4)/p(x_4)=2$, giving a log 2 factor of 0.301, which puts $p(x_4)=¼$ probability mass in bin "+0.3". The cumulative probability shown in FIG. 2 is a step function that monotonically increases from 0 to 1, incrementally adding probability mass $p(x_k)$ at each abscissa point $\log f(x_k)$.

Multiple Loci

An experiment can entail more than testing one locus. In DNA identification, multiple genetic loci are tested in a single reaction tube, generating data for a dozen or so loci simultaneously. Each tested locus l has its own locus genotype set $X_l$ and prior probability function $p_l$. After testing, the locus data can be analyzed to calculate the posterior probability $q_l$, factor $f_l$, and log factor $\log f_l$ functions.

DNA testing uses short tandem repeat (STR) loci, where genotypes are pairs of alleles differentiated by sequence length. The loci used in forensic identification have many different alleles that help distinguish between people. The loci are chosen to be genetically independent of one another, either residing on different chromosomes or far apart on the same chromosome. This biological independence confers statistical independence, where events at one locus convey no information about events at another locus. When testing multiple STR loci, independent results are multiplied together using the product rule.

The joint factor $f$ over all L independent locus tests is the product $$\prod_{l=1}^{L} f_l$$

of the locus factors $f_l$. The logarithm of a product is the sum of the logarithms. Therefore, $$\log f = \log\left(\prod_{l=1}^{L} f_l\right)$$

$$= \sum_{l=1}^{L} \log f_l$$

Thus the joint match statistic $\log f$ is the sum of the logarithmic locus factors $$\sum_{l=1}^{L} \log f_l.$$

The joint probability density u of a sum of independent random quantities having pmf's $u_1$, $u_2$, . . . , $u_L$ is the convolution of their pmf's. That is, $$u = u_1 * u_2 * \ldots * u_L$$

For discrete distributions, the convolution $u_1 * u_2$ is defined at value z as $$(u_1 * u_2)(z) = \sum_{y \in Y} u_1(y) \cdot u_2(z-y)$$

There is a corresponding integral formulation $$(u_1 * u_2)(z) = \int_{y \in Y} u_1(y) u_2(z-y) dy$$

for continuous or measurable distributions. Therefore, the joint non-contributor distribution for joint factor $f$ is readily computed by convolving the additive $\log f_l$ factor distribution functions of each locus l. Convolution is a built-in operation in many computer 12 programming languages, such as MATLAB (Natick, Mass.).

To implement this $\log f$ computation, first determine $\log f_l$ at each locus l. This can be done by partitioning the logarithmic factor abscissa (x-axis) into discrete bins of sufficiently fine resolution (e.g., milliban) so as to distinguish between most genotype events. Then, for each locus genotype $x_l$ with locus distributions $p_l(x_l)>0$ and $q_l(x_l)>0$, add ordinate (y-axis) probability mass $p_l(x_l)$ into the abscissa bin for $\log f_l(x_l)$ to form the $\log f_l$ pmf. Finally, convolve the separate $\log f_l$ locus pmfs to form the total $\log f$ pmf. Alternatively, one can convolve using the cumulative distribution function (CDF) of $\log f$.

Convolution can be performed on discrete or continuous functions, using probability densities or cumulative distributions. Since the cumulative distribution is the integral of probability density, appropriate differentiation of cumulative functions or integration of density functions provide a variety of convolution formulae. Convolution can also be accomplished by function transformation, using Fourier, Laplace, discrete Fourier, fast Fourier, polynomial, cosine, and other integration kernels (Nussbaumer 1982). Since the Fourier transform of a convolution is the product of the transformed functions, convolution can be done by Fourier inversion of products of functions in transform space.

Exclusionary Power

The $\log f$ non-contributor distribution is an inherent property of an inferred genotype, known before any match comparison is made to an exemplar genotype. Once posterior probability $q(x)$ has been determined from the data, the $\log f$ distribution can be calculated immediately. The non-contributor distribution describes the power of the genotype to statistically exclude non-contributors.

With informative data, posterior q(x) is different from prior p(x), i.e., p≠q. Then the average match statistic must be exclusionary, as shown next.

The average non-contributor log $f$ is the expected value $$E_p[\log f] = \sum_{x \in X} p(x) \log \frac{q(x)}{p(x)}$$

over every multi-locus genotype $(x_1, x_2, \ldots, x_L)$ in X. Since the logarithm of a reciprocal is the negative of the logarithm, this expected value equals $$= -\sum_{x \in X} p(x) \log \frac{p(x)}{q(x)}$$

The summation is the relative entropy of p and q, which equals the expected value under prior probability p of the logarithmic ratio of probability functions p and q $$= -E_p\left[\log \frac{p}{q}\right]$$

This expression is the negative value of the Kullback-Leibler divergence $KL_{pq}$ between p and q (Kullback and Leibler 1951), or $$= -D[p \| q]$$

Since $D[p\|q] > 0$ when p≠q (applying Jensen's inequality to the concave logarithm function), yields that $E_p[\log f] < 0$. So the expected non-contributor match value is exclusionary. A larger $KL_{pq}$ indicates greater exclusionary power, readily calculated as the non-contributor average of the log $f$ distribution.

Tail Probability

To determine the error, interest is drawn to the tail probability of the non-contributor pmf u(y) when y≥log α. This genotype specificity, easily calculated from function u(y), is precisely the size of the genotype error set $E_\alpha$.

To see why the tail probability $$\sum_{y \geq \log \alpha} u(y)$$

equals the size of the genotype error set $Pr\{x \in E_\alpha\}$, the u(y) tail probability is written as $$\sum_{y \geq \log \alpha} u(y) = \sum_{y \geq \log \alpha} \left[ \sum_{x \in \log f^{-1}(y)} p(x) \right]$$

expanding pmf u as a sum of prior probabilities p(x) over non-contributor genotypes x sharing log factor y. Writing out the inner summation for the set of genotypes x, yields $$= \sum_{y \geq \log \alpha} \sum_{\{x \in X | \log f(x) = y\}} p(x)$$

This gives the combined sum $$= \sum_{\{x \in X | \log f(x) \geq \log \alpha\}} p(x)$$

Exponentiating the logarithms on both sides of the summation's set condition inequality, the expression equals $$\sum_{\{x \in X | \log f(x) \geq \alpha\}} p(x)$$

Since $E_\alpha$ is the genotype error set $\{x \in X | f(x) \geq \alpha\}$, the set size that is obtained is $$= Pr\{x \in E_\alpha\}$$

A small tail probability value is consistent with the genotype not having contributed to the evidence. That is, the match statistic α would be far away from the bulk of non-contributor match scores. Therefore the error would be small, indicating that the observed match statistic is specific for the evidence genotype.

Contributor Distribution

Posterior Probability

The logarithmic distribution of match values for contributor genotypes can similarly be examined, now having posterior probability q(x). The layering of pairs (log q(x)/p(x), q(x)) for all genotypes x∈X is examined. For each abscissa location y=log $f(x)$, the ordinate contributor probability mass is $$v(y) = \sum_{\{x \in \log f^{-1}(y)\}} q(x)$$

The joint contributor distribution of the additive log factor is readily obtained by convolving the independent locus log factor pmfs.

Inclusionary Sums

The average contributor log $f$ match statistic is derived from a genotype as the expected value relative to posterior probability q as $$E_q[\log f] = \sum_{x \in X} q(x) \log \frac{q(x)}{p(x)}$$

This relative entropy is the KL divergence $$= D[q \| p]$$

The KL gives the expected inclusionary information in genotype pmf q, relative to prior p.

The tail probability of contributor pmf v(y) when y≥log α

$$\sum_{y \geq \log \alpha} v(y) = \sum_{\{x | f(x) \geq \alpha\}} q(x)$$

relates to the statistical sensitivity of the match statistic, and measures the size of set $E_\alpha$ after examining data $$= Pr\{E_\alpha | data\}$$

Suppose an exemplar genotype $x_K$ has factor $f(x_K)$. Then a large left posterior tail probability value $1-\Pr\{E_\alpha|data\}$ indicates high sensitivity, consistent with the genotype being a true contributor to the evidence.

Equality Formulation

Equalities can give more information and insight than inequalities. There are fundamental relationships between key measures and integrals that hold on the extreme set $E_\alpha$. These relationships are explored here.

Mean Factor Theorem

On any measureable set E, the determination of the average value of the measureable function $f$ with respect to a non-negative measure p is $$avg_p f = \frac{\underset{E}{sum} f \cdot p}{\underset{E}{sum} p}$$

When $f$ is a Bayes factor $q/p$, then $f \cdot p$ is $q/p \cdot p$; cancelling out prior p leaves the posterior distribution q, and so $$avg_p f = \frac{\underset{E}{sum} q}{\underset{E}{sum} p}$$

This function average on a set enables a simple description of the underlying mathematics and results for FMP.

False Match Probability

Rearranging Terms Yields $$\underset{E}{sum} p = \frac{\underset{E}{sum} q}{\underset{E}{sum} p}$$

The focus is the extreme subset $$E_\alpha = \{x \in X | f(x) \geq \alpha\}$$

of domain elements having extreme function values exceeding value $\alpha$.

In forensic DNA, this subset $E_\alpha$ is the set of genotypes x whose match statistic $f(x)$ is greater than or equal to the LR $\alpha = f(x_K)$ for a known person of interest K. The FMP is the measure of this extreme set $$\underset{E_\alpha}{sum} p$$

The FMP as a ratio can be written as $$\underset{E_\alpha}{sum} p = \frac{\underset{E_\alpha}{sum} q}{\underset{E}{sum}_p f}$$

Reciprocal Factor Bound

Since q is a probability distribution, on subset $E_\alpha$ the numerator inequality is $$\underset{E_\alpha}{sum} q \leq 1$$

Since an average cannot be less than a lower bound, on set $E_\alpha$ the denominator inequality is $$\alpha = \underset{E_\alpha}{\min} f \leq \underset{E_\alpha}{avg_p f}$$

The denominator inequality corresponds to the first inequality in the Markov-Turing proof, while the numerator inequality corresponds to the second one. In combination, they give the Markov-Turing result $$\underset{E_\alpha}{sum} p = \frac{\underset{E_\alpha}{sum} q}{\underset{E_\alpha}{avg_p f}} \leq \frac{1}{\alpha}$$

Shrinkage Factors

The Markov-Turing inequality can be rewritten as an equality formula, simply by replacing the two inequality steps in the proof with shrinkage factors bounded above by one. The shrinkage factors numerically explain the observed divergence (whether great or small) between an FMP and the generic match statistic reciprocal $1/\alpha$.

Numerator and denominator are algebraically separated as multiplicative factors $$\underset{E_\alpha}{sum} p = \frac{1}{\underset{E_\alpha}{avg_p f}} \cdot \underset{E_\alpha}{sum} q$$

Multiplying through by 1, written as $\alpha/\alpha$, yields $$\underset{E_\alpha}{sum} p = \frac{1}{\alpha} \cdot \frac{\alpha}{\underset{E_\alpha}{avg_p f}} \cdot \underset{E_\alpha}{sum} q$$

The Markov-Turing inequality is now re-expressed as an equality, with its two inequality steps written as shrinkage factors.

The LHS FMP is less than or equal to $1/\alpha$ because the RHS has $1/\alpha$ multiplied by two shrinkage factors, each guaranteed to be at most one, since $$\frac{\alpha}{\underset{E_\alpha}{avg_p f}} \leq 1$$

and $$\underset{E_\alpha}{sum} q \leq 1$$

Logarithmic Transformation

The probabilities and ratios have values between 0 and 1. A negative logarithm will transform these quantities to a positive order-of-magnitude scale. Applying the function "$-\log_{10}$" to both sides of the triple product equation gives $$-\log_{10} RME = \log_{10}\alpha + \log\left(\alpha^{-1} \cdot \operatorname*{avg}_{E_\alpha} {}_p f\right) - \log\left(\operatorname*{sum}_{E_\alpha} q\right)$$

The positively expressed FMP is represented as a baseline guarantee of log α plus two positive shrinkage terms.

The first shrinkage term $$\log\left(\alpha^{-1} \cdot \operatorname*{avg}_{E_\alpha} {}_p f\right)$$

expresses by how much the p-averaged match statistic $f$ on the extreme set $E_\alpha$ exceeds the minimum LR value of α. The second term $$-\log\left(\operatorname*{sum}_{E_\alpha} q\right)$$

measures the tail probability of posterior distribution q for genotypes having an LR≥α. When one or both of these shrinkage terms are large, the FMP may become much smaller than 1/α.

Tail Probability Ratio

The ratio of tail probabilities on the genotype error set $E_\alpha$ under different distributions (contributor vs. non-contributor) can be calculated directly without revisiting Markov-Turing proof. The average factor value on $E_\alpha$, weighted by the non-contributor measure p, is the ratio of sums (i.e., integrals)

$$\operatorname*{avg}_{E_\alpha} {}_p f = \frac{\operatorname*{sum}_{E_\alpha} f \cdot p}{\operatorname*{sum}_{E_\alpha} p}$$

But factor $f$ is the likelihood ratio q/p, so $f \cdot p = q$, yields the equality $$\operatorname*{avg}_{E_\alpha} {}_p f = \frac{\operatorname*{sum}_{E_\alpha} q}{\operatorname*{sum}_{E_\alpha} p}$$

That is, on $E_\alpha$ the average factor equals the ratio of posterior to prior tail probabilities.

Clearly on $E_\alpha = \{x \in X | f(x) \geq \alpha\}$ the factor α is less than or equal to $f(x)$, hence $$\alpha \leq \operatorname*{avg}_{E_\alpha} {}_p f.$$

Therefore, with $\alpha = q(x_K)/p(x_K)$ for a known exemplar K, $$\alpha \leq \operatorname*{avg}_{E_\alpha} {}_p f = \frac{\operatorname*{sum}_{E_\alpha} q}{\operatorname*{sum}_{E_\alpha} p}$$

or $$\alpha \leq \frac{\operatorname*{sum}_{E_\alpha} q}{\operatorname*{sum}_{E_\alpha} p}$$

This corollary of the mean factor theorem shows that a match statistic α is more conservative than the ratio of its tail probabilities.

Population Adjustments

Co-Ancestry Correction

All people share a common ancestry, more so in closely related populations. Therefore, human genotypes are not entirely independent of each other. The usual Hardy-Weinberg equilibrium population probability for a genotype ij $$Pr\{X = ij\} = \begin{cases} p_i^2, & i = j \\ 2 p_i p_j, & \text{otherwise} \end{cases}$$

that assumes independent mating therefore requires some adjustment.

A simple and effective correction is to introduce a co-ancestry coefficient θ that measures the degree of inbreeding within a population. Then the prior genotype probabilities become (Ott 1991)

$$Pr\{X = ij | \theta\} = \begin{cases} p_i^2 + \theta p_i(1 - p_i), & i = j \\ 2(1 - \theta) p_i p_j, & \text{otherwise} \end{cases}$$

accounting for an increase in homozygote (i=j) genotypes, with a commensurate decrease in heterozygotes (i≠j).

Population Substitution

Bayesian genotype inference updates population prior p(x) to a posterior q(x). This update is mediated though a likelihood function $$l(x) = Pr\{\text{data} | X = x, \ldots\}$$

based on observed DNA data, where $$q(x) \propto l(x) p(x)$$

So for a different population $p_o(x) \neq p(x)$ having different allele frequencies, the posterior $q_o(x) \neq q(x)$ is different as well. One genotype posterior $q_o(x)$ can be transformed based on prior $p_o(x)$ to a new q(x) based on p(x). This is easily done through the likelihood function l using Bayes theorem by writing posterior function q as $$q(x) = \frac{l(x) p(x)}{\sum_{y \in X} l(y) p(x)}$$

for any prior function p. In a vectorized computer 12 language, q can be calculated over the entire domain x∈X in one step.

In the MATLAB programming language, for example, likelihood 1 and prior p column vectors are combined as l.*p over l'*p to produce the posterior genotype probability vector q. In practice, one can exhaustively compute a genotype $q_o(x)$ using any prior $p_o(x)$, and use Bayes theorem to swap in a new population p(x) later on. Changing populations does not necessitate extensive genotype re-computation.

Case Example

Sexual Assault

On New Year's night, 1 Jan. 2014, a woman was sexually assaulted when walking home through a park at 3 am in Southampton, England. The police collected vaginal swabs from the victim, and submitted them to a forensic laboratory for DNA testing with an SGMplus® kit (Applied Biosystems, Foster City, Calif.). Searching the DNA evidence against England's national DNA database (NDNAD) identified 13 candidate suspects based on allele similarity. Other non-biological factors, such as geographical location, singled out homeless Stuart Ashley Burton as the likely perpetrator.

Cybergenetics (Pittsburgh, Pa.) applied the TrueAllele® Casework software to the SGMplus data, separating out the genotypes of two contributors. The major 85% contributor matched the victim with a statistic of a trillion. Comparing the minor 15% genotype distribution q(x) with Burton's known genotype $x_k$, relative to a Caucasian population p(x), gave a Bayes factor $f(x_K)$ of 67,890 with log $f(x_K)$=4.8318 ban.

Figure 3:
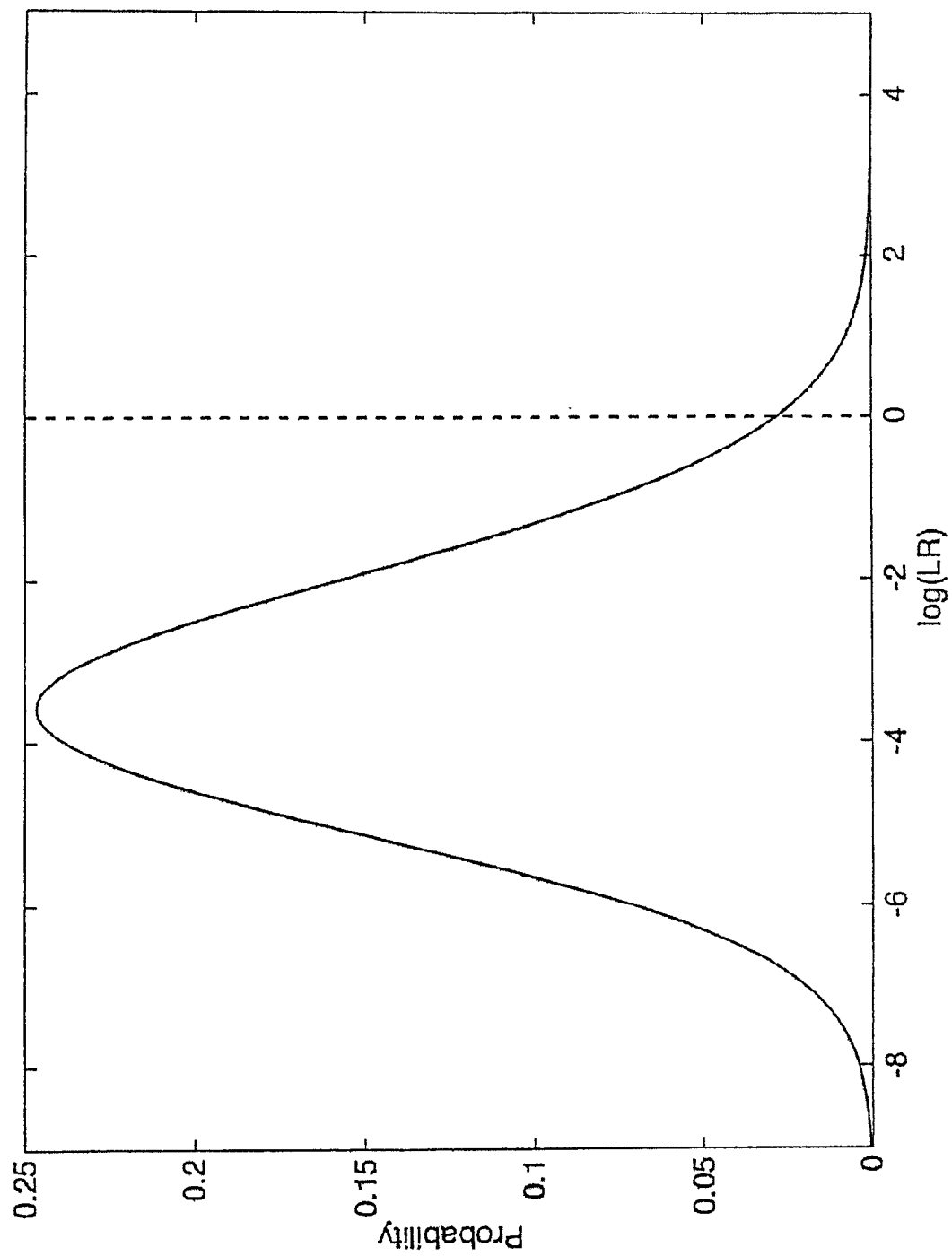
FIG. 3 shows a joint non-contributor distribution for a genotype separated from DNA mixture evidence in the Southampton case, as computed by the TrueAllele computer and displayed in the user interface.

TrueAllele can bin locus log $f_l(x)$ values for genotypes x, weighted by prior probabilities $p_l(x)$, to form non-contributor densities $u_l(y)$ along a y=log $f$ scale. Convolving these $u_l$ locus densities will produce a joint non-contributor distribution u(y), shown in FIG. 3. This u distribution has an average exclusionary power $$E_p\left[\log\frac{q(x)}{p(x)}\right]$$

of $KL_{pq}$=−3.4397 ban, with a standard deviation of 1.6253 ban.

False Match Probability

Burton's $f(x_K)$ match statistic of 67.9 thousand has log $f(x_K)$ of 4.8318 ban, which gives a right tail probability of $0.9197 \times 10^{-6}$, or $1/1,087,000$. Therefore, the chance that a non-contributor (someone who did not contribute their DNA to the vaginal swab evidence) has a match statistic of 67.9 thousand or more, is one in 1.087 million. This exact FMP is a number 16 times more specific than the generic $1/\alpha$ reciprocal error estimate of one in 67.9 thousand. The two inequalities in the Markov-Turing derivation show the source of this improvement in the FMP estimate.

The first inequality (1) says that the smallest factor $f(x)$ on the genotype error set $E_\alpha=\{x \in X | f(x) \geq \alpha\}$ cannot exceed the average factor on that set, or $$\alpha = f(x_K) = \min_{E_\alpha} f \leq avg_p f = \frac{\sum_{x \in E_\alpha} f(x)p(x)}{\sum_{x \in E_\alpha} p(x)}$$

Substituting into this expression the values of $f(x_K)$ and the two sums in this case yields $$f(x_K) = 67,890 \leq 225,900 = \frac{0.2078}{0.9197 \times 10^{-6}}$$

A larger genotype error set $E_\alpha$ gives a longer non-contributor tail $$\sum_{x \in E_\alpha} p(x)$$

and a potentially greater discrepancy between min $f$ and avg $f$. Here the avg $f$/min $f$ relative gain is 3.3274.

The second Markov-Turing inequality (2) notes that the contributor distribution tail probability on $E_\alpha$ cannot exceed 1, $$\sum_{x \in E_\alpha} q(x) \leq 1$$

In this example the contributor tail has mass $$\sum_{x \in E_\alpha} q(x) = 0.2175$$

so its reciprocal value 4.5969 gives the "FMP to 1/LR" gain at this second step. Short contributor tails will yield higher gains at this stage.

Combining the Two Inequality Gains Gives gain=(gain 1)(gain 2)

=(3.3274)(4.5969)

=15.2959

This value approximates the observed overall 1/LR to FMP ratio of 16.0162. (When θ is zero, the predicted and observed gains are almost identical.) In this case, the 16-fold improvement in the error bound from the automatic 1/LR=1/67,890 to the more exact FMP=1/1,087,000 instills greater confidence that the match statistic is not falsely including an innocent person.

Verifying Accuracy

To verify FMP accuracy, a cumulative distribution for the evidence genotype was independently calculated by Monte Carlo simulation. Ten thousand non-contributor genotypes were randomly drawn from a Great Britain Caucasian (GBC) population. The TrueAllele VUIer software compared the evidence genotype with these randomly simulated exemplars, relative to a GBC population, to calculate match statistics and their base 10 logarithms. A co-ancestry theta of 1% was used.

Figure 4:
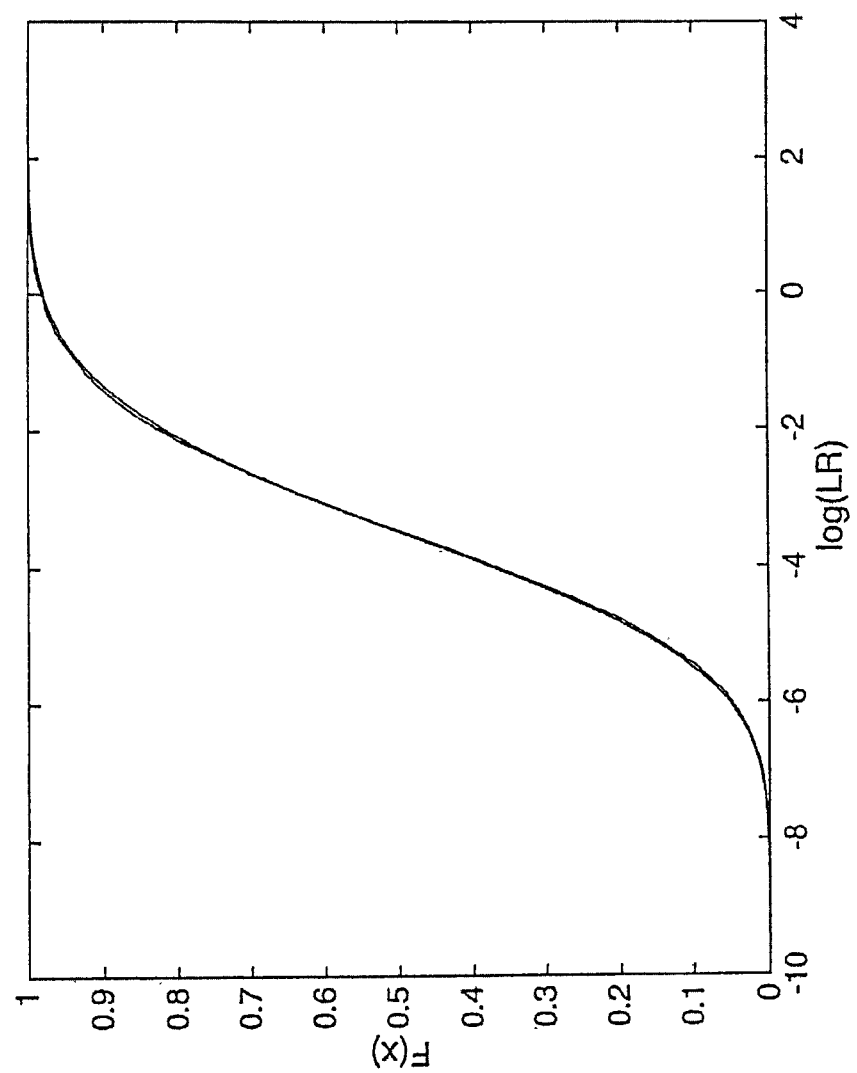
FIG. 4 shows CDFs for convolution-based log $f$ values (blue) and Monte Carlo simulated values (red).

CDFs for the convolution-based log $f$ values (blue) and the Monte Carlo simulated values (red) are shown in FIG. 4. The two CDF curves are quite similar. A Kolmogorov-Smirnoff test rejected the null hypothesis that the two distributions are statistically different (p=0.2475). The K-S statistic was 0.0102, with a critical value of 0.0136.

The two distributions are statistically indistinguishable. But whereas convolving probability functions gives exact values throughout the entire log factor range, Monte Carlo approximation has limited sampling in the sparse probability tail regions. Since error determination focuses on the tail regions, exact convolution is preferable to Monte Carlo simulation for determining accurate FMP probability.

Database Identification

When a DNA database search of evidence returns multiple people k=1, ..., K, they can be differentiated by their match statistic. For each retrieved known genotype $x_K$, determining the posterior-to-prior probability ratio $q(x_K)/p(x_K)$ gives a Bayes factor of $f(x_K)$ that can be used to compare the retrieved genotypes (Table 2, column 2).

Figure 5:
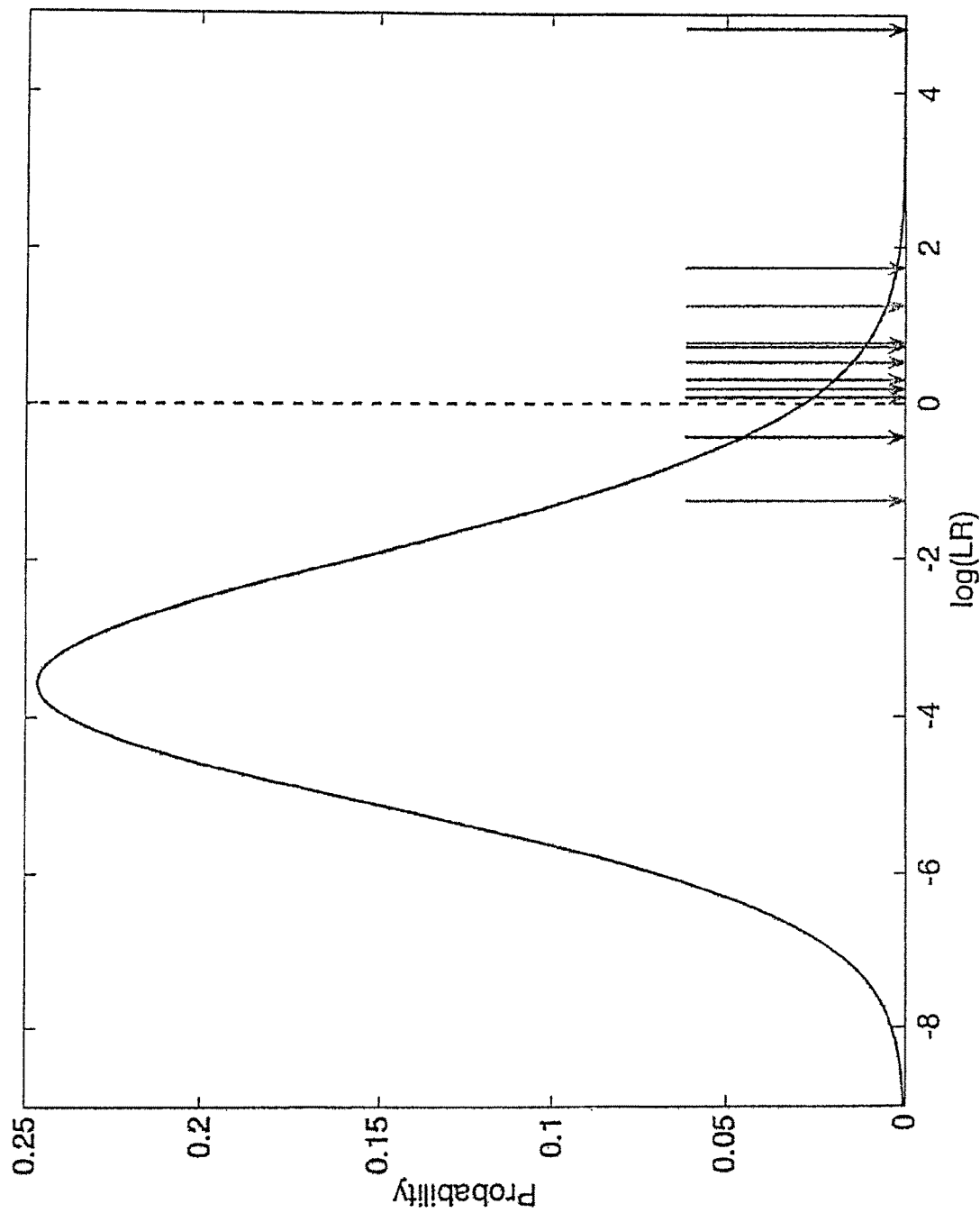
FIG. 5 shows the joint non-contributor distribution (curve) in the Southampton case; arrows (bars) indicate the log factor values of retrieved DNA database genotypes.

In the Southampton rape case, the genotypes show largely positive log $f(x)$ values (Table 2, column 3 & FIG. 5). This is because they were all retrieved from a database search through allelic similarity to the same evidence genotype $q(x)$. However, relative to the evidence, Burton's genotype has a log $f$ value of 4.8318. This value is over 4 ban greater the 0.4731 ban match statistic average of the other twelve, and over 3 ban away from the largest neighboring value of 1.7455 ban (Table 2, column 3).

The FMP can provide additional information useful for differentiating between similar genotypes found from a database search. The FMPs of the 12 less likely suspects range from 1 in 10, to 1 in 800 (Table 2, last column). However, Burton's log $f$ error is 1 in 1.087 million, which is highly specific. This FMP shows that it is extremely unlikely that he is a non-contributor whose genotype produced the 67,890 match statistic by chance.

Based on the DNA match statistics, and other evidence, Burton pleaded guilty to the New Year's Day sexual assault. He was sentenced to twelve years in prison.

Measure Theory

The Lebesgue theory of measurable sets, functions and integrals generalizes continuous functions and Riemann integration to handle pathological situations (Wheeden and Zygmund 1977). Lebesgue measure and integration work with finite and infinite sets, over discrete and continuous domains, and eliminate technical issues involving sets of measure zero and infinite discontinuities.

General Measures

For a set X, a σ-algebra Σ of subsets of X contains X, and is closed under set complementation and countable set unions. A measure μ is a nonnegative function on measureable subsets E in Σ for which $\mu(\Box E_K)=\Sigma\mu(E_K)$, whenever $\{E_K\}$ is a countable family of disjoint sets in Σ.

A measure space is a triple (X, Σ, μ). A real-valued function $f(x)$ defined for x in a measureable set E in Σ is a measureable function when $\{x \in E | f(x) > \alpha\}$ is a measureable set for all finite real numbers $\alpha \in \Box$. The Lebesgue integral $\int_E f d\mu$ of a measureable function $f$ over a measureable set E with respect to measure μ is more robust than its Riemann counterpart, and enjoys many useful convergence properties.

Pushforward Measure

Let (X, Σ, μ) be a measure space, and $f$ a measureable function from X to $\Box^1$. Let ($\Box$, $\mathscr{B}$) be the space of real numbers with the Borel σ-algebra $\mathscr{B}$. Then the pushforward measure $f_*(\mu)$ is a nonnegative measure defined as $$f_*(\mu)(B)=\mu(f^{-1}(B))$$

for every Borel set B in $\mathscr{B}$. The resulting measure space ($\Box$, $\mathscr{B}$, $f_*(\mu)$) is the one induced on $\Box$ by measure space (X, Σ, μ) and function $f$.

In particular, for any $\alpha \in \Box$, consider the half infinite interval $$I(\alpha,\infty)=\{y \in \Box | y > \alpha\}$$

Taking the inverse image under function $f$, yields $$E_\alpha = f^{-1}(\alpha,\infty)=\{x \in X | f(x) > \alpha\}$$

is the subset of X having $f(x) > \alpha$. The measure of this subset $E_\alpha$ $$\mu(E_\alpha)=\mu(f^{-1}(\alpha,\infty))$$

describes the size of $E_\alpha$. Given a measure space (X, Σ, μ), the pushforward measure $f_*(\mu)$ specifies a distribution function on $\Box$.

When μ is a probability measure, so that μ(X)=1, $$\mu(E_\alpha)=\mu(f^{-1}(\alpha,\infty))$$

$$=f_*(\mu)(\alpha,\infty)$$

$$=\int_\alpha^\infty df_*(\mu)$$

Thus subset probability $\mu(E_\alpha)$ is pushed forward from (X, Σ, μ), and equals the tail probability $\int_\alpha^\infty df_*(\mu)$ on the infinite interval (α, ∞) in the measure space ($\Box$, $\mathscr{B}$, $f_*(\mu)$). On any probability space (X, Σ, μ), the pushforward measure for $f$ induces a probability distribution function on the real line.

General FMP

The section on "Tail probability" showed that tail probability $$\sum_{y \geq \log \alpha} u(y)$$

equals the genotype error set probability Pr{x∈$E_\alpha$}. This equality follows immediately from measure theory when the tail probability is defined through a pushforward measure.

In general, pushing $f$ forward from X to $\Box$ reduces the problem of finding a measure $\mu(E_\alpha)$ in a multidimensional probability space (X, Σ, μ) to that of calculating an integral in the one dimensional probability space ($\Box^1$, $\mathscr{B}$, $f_*(\mu)$). This integral is the right tail probability $\int_\alpha^\infty df_*(\mu)$ of $f$ starting from point α, which is the same as one minus the cumulative distribution $\int_{-\infty}^\alpha df_*(\mu)$ of $f$ ending at α. The pushforward dimension reduction translates subset probability in (X, ∈, μ) into a simpler integral over $\Box^1$.

When the measure μ is the prior distribution p(x), the pushforward measure $f_*(p)$ describes the non-contributor factor distribution. When μ is the posterior q(x), pushforward measure $f_*(q)$ gives the contributor factor distribution. Using log $f$ in place of $f$ pushes forward onto $\Box$ the corresponding log factor distribution.

Operation

A preferred way to operate a method for determining probability of error in identifying evidence is comprised of the steps:

a. Obtaining Prior and Posterior Probability Distributions from a Plurality of Independent Tests Conducted on an Item of Evidence;

Each test has a set of possible outcomes. Prior to conducting the tests, there is a prior probability distribution of these outcomes. The tests are conducted, developing data for each test. Using Bayes theorem, the observed data update belief to produce a posterior probability distribution over the outcomes. With DNA analysis, STR tests are analyzed by Bayesian software such as TrueAllele to give genotype probabilities.

b. Entering the Probability Distributions into a Non-Transitory Memory of a Computer;

The prior and posterior probabilities for every test can be entered as input into the computer 12. Alternatively, these probabilities may already reside in memory 14 from earlier computer 12 operations.

c. For Each Test, Forming a Factor Distribution from the Test's Probability Distributions with the Computer Using a Software Program 16 Stored in the Non-Transitory Memory of the Computer;

Computer software can calculate a test's factor as the ratio of posterior to prior probability for each possible outcome, and then calculate the logarithm of this ratio. At each test l, partition the logarithmic factor x-axis abscissa into discrete bins of sufficiently fine resolution (e.g., milliban) so as to distinguish between most outcome events. Then, for each test outcome $x_l$ with test distributions $p_l(x_l) > 0$ and $q_l(x_l) > 0$, add a y-axis amount of prior probability mass $p_l(x_l)$ into the x-axis abscissa bin at log $f_l(x_l)$. When done, the bin distribution forms the prior-weighted log $f_l$ pmf.

d. Convolving the Independent Factor Distributions to Form a Joint Factor Distribution by the Computer Using the Software Program 16;

The computer software program 16 convolves the separate log $f_l$ test pmfs. Because the tests and their distributions are independent, the convolution forms the total log $f$ pmf. The computer 12 weights the log $f$ values by prior $p(x)$ to form the non-contributor log $f$ distribution, which provides exclusionary information about the evidence. It weights by posterior $q(x)$ to form the contributor distribution, which provides inclusionary information about the evidence.

e. Calculating a Tail Probability from the Joint Factor Distribution by the Computer Using the Software Program 16 to Determine a Probability of Error in Identifying the Evidence;

The computer program adds together the probability amounts in the x-axis bins, starting from point α, to numerically calculate the tail probability $$\sum_{y \geq \log \alpha} u(y).$$

This calculated value is the false match probability of error $\Pr\{x \in E_\alpha\}$.

f. Storing the Probability of Error in the Non-Transitory Memory of the Computer; and Once the probability of error has been calculated, this error value is stored in computer memory 14. The value can be retrieved later on via a computer screen, graphical display, hardcopy printout, email message, database application, or network communication.

g. Reporting the Probability of Error from the Computer to a Party Interested in Identifying the Evidence.

The probability of error can be reported to help identify the evidence. In a forensic DNA report, the error language can be stated as: "A false positive would occur if a non-contributor (someone who didn't contribute their DNA) to the evidence had a match statistic of (state the $\alpha = f(x_K)$ factor value for exemplar K) or more. The chance of a false positive for this comparison is (state the calculated $\Pr\{x \in E_\alpha\}$ error value)."

Applications

Computing Capability

The claimed invention has application whenever a likelihood ratio is used, providing a rapid, accurate and reusable way to calculate the error of the LR. The method is accurate because exact numerical calculation is done to within any desired resolution over the entire range of log(LR) values. The method is rapid because function convolution is very fast, and the invention transforms multiplicative LR distributions into additive log(LR) distributions that can be convolved.

Whereas the prior art entails recalculation of tail probabilities with every new exemplar's factor value, the invention precomputes the entire evidence log(LR) distribution, relative to prior or posterior probability. This precomputation enables reuse of the distribution when comparing the evidence with different exemplars. Such multiple comparisons are done with the assessment of genotypes retrieved from DNA databases.

The invention permits error determination over much larger type spaces than the prior art. STR multiplexes in DNA identification have between 5 to 50 independent locus tests. Each test produces data for about 10 common allele sizes, and 100 less common alleles. Genotypes are unordered pairs of such alleles, so the full model space for one locus can have 1000's of possible genotype values. With 25 independent loci there can then be $1000^{25}$, or $10^{75}$, possible joint genotype values to assess.

In the prior art, simple genotyping methods consider relatively few of these possibilities, and so examine only a small portion of the genotype space. This limited examination can give incorrect LR values, but greatly reduces the time to calculate LR and tail probability errors. When examining an entire genotype space, however, such limited approaches fail to calculate LR error in an acceptable amount of time.

In contrast to this limited determination of genotype, LR, and error, the claimed invention can calculate error even when considering all possible genotype values. A computer 12 quickly assembles the exact log(LR) distribution for each locus test through a rapid binning procedure. It then uses a fast convolution procedure to assemble the separate additive tests into a composite log(LR) joint distribution. This fast divide-and-conquer procedure over independent loci enables a complete examination of LR error, which the computer 12 can accomplish in seconds.

Forensic Science

Forensic identification entails producing a match statistic to quantify the strength of match of evidence items, relative to coincidence. Across all forensic disciplines, the scientifically accepted match statistic is the likelihood ratio (Aitken and Taroni 2004). Therefore error determination of LR values through rapid and accurate tail probabilities can be universally applied throughout all of forensic science.

Without limitation, representative disciplines of forensic identification include DNA testing, fingerprint comparison, glass evidence, blood spatter, firearms and toolmarks, and impression evidence such as tire or foot marks. Every forensic discipline involves LR statistics, so the error determination of the claimed invention applies to reported LR values in all of forensic identification.

The invention determines contributor and non-contributor LR distributions in advance of making any comparison with an exemplar. These match statistic distributions describe the probative force of forensic evidence. The average log(LR) value of the non-contributor distribution measures the exclusionary power of the evidence. The average log(LR) value of the contributor distribution (or KL statistic) measures the inclusionary power of the evidence. These evidence measures can help in determining the utility of evidence, since a greater ability to include or exclude possibilities provides more identification informative.

Criminal Justice

The claimed invention is useful in criminal investigation. When forensic modalities produce an investigative lead, the probative value of that lead can be expressed as a LR. The error of that LR describes the chance of making a mistake. An exact error estimate helps in predicting how useful an item of evidence may be in an investigation. With DNA databases, retrieved exemplars may be similar, and so their false match probabilities offer a way to rank the genotypes for use as possible leads.

In court, the claimed invention assists a trier of fact in assessing forensic or other evidence. The error gives a probability of making a mistake, for example associating the wrong person with a crime. Jurors and judges may not be conversant with Bayesian reasoning and likelihood ratios, but non-experts understand the frequency of error. The invention provides a probability of identifying someone unconnected to the evidence, despite a positive log(LR) match statistic. That chance of error, can help implicate guilty defendants when low, and exonerate innocent defendants when high.

Any party can apply the invention to help undermine weak forensic evidence. Calculating a false match probability on a reported match statistic can show when the evidence is less (or more) informative than claimed. With DNA testing, computer programs produce locus genotype probabilities on mixtures and other samples. By entering these genotype probabilities and the reported LR values, the invention's computer 12 program can calculate error rates for the LR values generated by other programs.

Other Applications

The claimed invention has utility in biometrics (e.g., facial recognition, iris identification, etc.) by providing an error probability whenever a likelihood ratio is calculated. The invention's error rate is useful in intelligence gathering, for example in image recognition, pattern detection, and document identification. The LR is used in natural language processing, where the claimed invention can determine error rates.

Genetic testing produces likelihood ratios, so the invention can provide error probabilities for LR values that are customized to the genetic evidence. Parentage testing (whether paternal or maternal) reports an LR, known as the "paternity index," for which the invention can calculate a false match probability. More general kinship analysis for identifying missing persons also entails prior and posterior genotype probability, so the invention can calculate error probability in those applications.

In medical testing and diagnosis, likelihood ratios help determine the extent to which a test result is associated with a disease. The LR helps clinicians assess a positive test result, ascribing the outcome to a specific disease or to chance. The invention calculates an error probability for an LR test outcome, framing the error in understandable frequency terms for misdiagnosing a patient in the population. Customizing the LR and error to specific patient populations (e.g., by swapping in appropriate prior probability) can lead to more accurate diagnosis when using the same clinical data.

The invention has consumer applications, such as determining error when matching customers to products. In finance, the invention can help assess market trends, for example by comparing past and future probability assessments, and calculating error for the statistics of a particular hypothesis or decision.

CONCLUSION

In identification science there can be a very large (finite or infinite) number of possible types. Observable types that exist in the physical world can be conceptualized as random samples drawn from this type space. Probability and information statements made about observed types refer to the full sample space of all possible types.

A prior probability distribution describes the chance of observing a type before examining data. A posterior distribution over the type space updates these probabilities based on examined data. The Bayes factor of a type in the sample space is a ratio (where defined) of posterior to prior probabilities. The log factor is an additive information measure of Bayes update for a type.

When stating a factor for a type exemplar relative to evidence, there is a chance of false match error. Specifically, this error is the probability of misidentifying a non-contributor type as a contributor because it coincidentally has a factor value at least as large as a match statistic. This probability of falsely matching the wrong exemplar by chance is the FMP. This error can be quantified by calculating the size of the subset of misidentified types having spuriously large factors.

The FMP can be costly to calculate exactly on a very large type space. However, when a type is formed from a collection of independent subtypes, the factor is a numerical product of the subtype factor values. The logarithm function transforms such products into sums. Therefore, convolution of the additive log factor subtype distributions efficiently computes their joint log factor distribution. Evaluating the tail probability of this joint distribution beyond a fixed log factor value gives the measure of the type subset showing false matches.

A trier of fact does not want to make a mistake by wrongly convicting an innocent person. Most jurors do not know Bayes theorem or logarithms. Few have studied mathematical probability, and fewer still have learned conditional probability. They rarely know about likelihood (the probability of data given a hypothesis), much less the likelihood ratio that contrasts two competing hypotheses. But they do understand error rates, and they want to avoid making an error.

Considering all the people in the world, what is the chance that a reported match statistic identifies the wrong person? DNA mathematics lets us randomly embed the seven and a half billion ($10^{10}$) people in the world into a dense space of a trillion trillion ($10^{24}$) possible genotypes. Population genetics can estimate prior genotype probability, while Bayesian update on evidence data can produce a posterior genotype distribution. Prior and posterior combine to give a Bayes factor function over the entire genotype space.

The inverse of the factor function connects extreme match values to a corresponding error subset of types. The one dimensional tail probability of extreme match values gives the multidimensional measure of non-contributor types. Actual objects in the physical world have types that are samples from the full type space. To determine a false match probability relative to all the people in the world, it is easier to reduce the problem to calculating a univariate function and its tail probability. Logarithmic transformation of independent factors permits rapid calculation of these tail probabilities through function convolution.

The LR summarizes the probative value of evidence in forensic identification. The FMP puts an error rate to that LR value, customized to the evidence in a particular case. Both numbers are important to a trier of fact—the LR's strength of match, and the FMP's chance of error. While 1/LR is always an upper bound on LR error, calculating the FMP can provide an exact estimate of misidentification frequency.

The FMP gives additional error rate information about an LR match statistic, simply expressed as the chance of making a mistake.

Table 1. Forming log $f$ values from prior and posterior probability.

TABLE 1

Forming log f values from prior and posterior probability.

| Type x | Prior p(x) | Posterior q(x) | Factor f(x) | log factor log f(x) |
|---|---|---|---|---|
| 1 | 0.20 | 0.10 | 0.5 | −0.301 |
| 2 | 0.30 | 0.15 | 0.5 | −0.301 |
| 3 | 0.25 | 0.25 | 1.0 | 0.000 |
| 4 | 0.25 | 0.50 | 2.0 | 0.301 |

Table 2. The DNA match statistics and error probabilities in the Southampton case. Each row represents a different retrieved DNA database genotype, with "SB" the accused. The last column's "one in" value is the reciprocal of the false match probability in the adjacent column.

TABLE 2

The DNA match statistics and error probabilities in the Southampton case. Each row represents a different retrieved DNA database genotype, with "SB" the accused. The last column's "one in" value is the reciprocal of the false match probability in the adjacent column.

| Item | LR | log(LR) | Pr(error) | one in: |
|---|---|---|---|---|
| 1 | 1/(17.7) | −1.2485 | 0.09155110 | 11 |
| 2 | 1/(2.72) | −0.4339 | 0.03595410 | 28 |
| 3 | 1.21 | 0.0824 | 0.01818210 | 55 |
| 4 | 1.54 | 0.1878 | 0.01569030 | 64 |
| 5 | 2.01 | 0.3025 | 0.01330630 | 75 |
| 6 | 3.35 | 0.5248 | 0.00958381 | 104 |
| 7 | 3.35 | 0.5248 | 0.00958381 | 104 |
| 8 | 5.21 | 0.7166 | 0.00713871 | 140 |
| 9 | 5.90 | 0.7709 | 0.00655932 | 152 |
| 10 | 17.8 | 1.2513 | 0.00297871 | 336 |
| 11 | 17.9 | 1.2535 | 0.00296855 | 337 |
| 12 | 55.6 | 1.7455 | 0.00123809 | 808 |
| SB | 67,900 | 4.8318 | 0.00000092 | 1,090,000 |

The following works are incorporated by reference into this application:

References, all of which are incorporated by reference herein.

Aitken, C. G. and F. Taroni (2004). *Statistics and the Evaluation of Evidence for Forensic Scientists*. Chicester, UK, John Wiley & Sons.

Corradi, F. and F. Ricciardi (2013). "Evaluation of kinship identification systems based on short tandem repeat DNA profiles." *Journal of the Royal Statistical Society: Series C (Applied Statistics)* 62(5): 649-668.

Dørum, G., Ø. Bleka, et al. (2014). "Exact computation of the distribution of likelihood ratios with forensic applications." *Forensic Science International: Genetics* 9: 93-101.

Feller, W. (1968). *An Introduction to Probability Theory and Its Applications*. New York, John Wiley & Sons.

Gill, P., J. Curran, et al. (2008). "Interpretation of complex DNA profiles using empirical models and a method to measure their robustness." *Forensic Science International: Genetics* 2(2): 91-103.

Good, I. J. (1950). *Probability and the Weighing of Evidence*. London, Griffin.

Kruijver, M. (2015). "Efficient computations with the likelihood ratio distribution." *Forensic Science International: Genetics* 14: 116-124.

Kruijver, M., R. Meester, et al. (2015). "p-Values should not be used for evaluating the strength of DNA evidence." *Forensic Science International: Genetics* 16: 226-231.

Kullback, S. and R. A. Leibler (1951). "On information and sufficiency." *Ann Math Stat* 22(1): 79-86.

MacKay, D. J. (2003). *Information Theory. Inference and Learning Algorithms*. Cambridge, UK, Cambridge University Press.

Nothnagel, M., J. Schmidtke, et al. (2010). "Potentials and limits of pairwise kinship analysis using autosomal short tandem repeat loci" *Int J Legal Med* 124: 205-215

Nussbaumer, H. J. (1982). *Fast Fourier Transform and Convolution Algorithms*. New York, Springer-Verlag.

O'Hagan, A. and J. Forster (2004). *Bayesian Inference*. New York, John Wiley & Sons.

Ott, J. (1991). *Analysis of Human Genetic Linkage*. Baltimore, Md., The Johns Hopkins University Press.

Perlin, M. W., M. M. Legler, et al. (2011). "Validating TrueAllele® DNA mixture interpretation." *J Forensic Sci* 56(6): 1430-1447.

Slooten, K.-J. and T. Egeland (2014). "Exclusion probabilities and likelihood ratios with applications to kinship problems." *Int J Legal Med* 128(3): 415-425.

Slooten, K.-J. and T. Egeland (2015). "Exclusion probabilities and likelihood ratios with applications to mixtures." *Int J Legal Med* 130(1): 39-57.

Taroni, F., S. Bozza, et al. (2016). "Dismissal of the illusion of uncertainty in the assessment of a likelihood ratio." *Law Probability and Risk* 15 (2): 1-18.

Taylor, D., J. Buckleton, et al. (2015). "Testing likelihood ratios produced from complex DNA profiles." *Forensic Science International: Genetics* 16: 165-171.

Wheeden, R. L. and A. Zygmund (1977). *Measure and Integral: An Introduction to Real Analysis*. New York, Marcel Dekker.

The invention claimed is:

1. A method for performing a criminal investigation comprising the steps of:
   obtaining a biological sample of a DNA mixture having DNA of at least 2 individuals;
   comparing an evidence genotype from the DNA mixture with a known exemplar genotype to form a comparison;
   expressing a probative value of a lead based on the evidence genotype as a likelihood ratio;
   determining an error of the likelihood ratio; and
   predicting how useful the lead may be in the investigation based on the error.

2. A method for considering evidence of a crime comprising the steps of:
   obtaining a biological sample of a DNA mixture having DNA of at least 2 individuals from a fire arm;
   comparing an evidence genotype from the DNA mixture with a known exemplar genotype to form a comparison;
   determining genotype probabilities and associated likelihood ratio values with respect to evidence from the fire arm and the comparison;
   calculating error rates for the likelihood ratio values; and
   assessing evidence based on its error rates for the likelihood ratio values.

3. A method for recognizing an individual comprising the steps of:
   determining a likelihood ratio from facial recognition of an individual;
   calculating an error probability of the likelihood ratio; and
   finding a risk of incorrectly identifying the individual based on the error probability.

4. The method of claim 1 wherein the comparing step includes the step of determining a match statistic from the comparison.

5. The method of claim 4 wherein the predicting step includes the step of identifying the evidence genotype is associated with a contributor to the DNA sample.

* * * * *